United States Patent
Gogin et al.

(10) Patent No.: US 10,971,263 B2
(45) Date of Patent: *Apr. 6, 2021

(54) METHODS AND APPARATUS FOR RECORDING ANONYMIZED VOLUMETRIC DATA FROM MEDICAL IMAGE VISUALIZATION SOFTWARE

(71) Applicant: General Electric Company, Schenectady, NY (US)

(72) Inventors: Nicolas Gogin, Buc (FR); Jerome Knoplioch, Buc (FR)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/565,040

(22) Filed: Sep. 9, 2019

(65) Prior Publication Data

US 2020/0005930 A1 Jan. 2, 2020

Related U.S. Application Data

(63) Continuation of application No. 15/232,397, filed on Aug. 9, 2016, now Pat. No. 10,452,812.

(51) Int. Cl.
 *G16H 30/20* (2018.01)
 *G16H 30/40* (2018.01)
 *G06F 21/62* (2013.01)

(52) U.S. Cl.
 CPC ......... *G16H 30/20* (2018.01); *G06F 21/6254* (2013.01); *G16H 30/40* (2018.01)

(58) Field of Classification Search
 None
 See application file for complete search history.

(56) References Cited

U.S. PATENT DOCUMENTS

| 8,315,481 B2 | 11/2012 | Hayashi |
| 2008/0177176 A1 | 7/2008 | Basterrechea et al. |
| 2009/0175411 A1* | 7/2009 | Gudmundson ...... G06K 9/3241 378/57 |

(Continued)

FOREIGN PATENT DOCUMENTS

WO 2013123085 8/2013

OTHER PUBLICATIONS

Visceral, "Initial report on legal, ethical, and privacy requirements for data distribution, focussing on Competition 1", 2013 (Year: 2013).*

(Continued)

*Primary Examiner* — Dennis W Ruhl

(57) ABSTRACT

Methods and apparatus for recording anonymized volumetric data from medical image visualization software are disclosed. An example apparatus includes an image anonymizer to anonymize a medical image outside of a region of interest based on an extraction parameter by degrading the medical image outside a region corresponding to the region of interest and maintaining a resolution of the medical image inside the region corresponding to the region of interest, the extraction parameter based on at least one of an image capture parameter or an instruction from a remote system; and an archive generator to generate a compressed local archive based on the anonymized medical image.

17 Claims, 8 Drawing Sheets

(56) References Cited

U.S. PATENT DOCUMENTS

| | | | |
|---|---|---|---|
| 2013/0060579 A1* | 3/2013 | Yu | G06Q 10/10 |
| | | | 705/3 |
| 2013/0208955 A1* | 8/2013 | Zhao | G06T 7/0012 |
| | | | 382/128 |
| 2013/0251219 A1 | 9/2013 | Mehta | |
| 2016/0224805 A1 | 8/2016 | Patti | |
| 2016/0307063 A1 | 10/2016 | Bright et al. | |

OTHER PUBLICATIONS

Leung, K.Y. et al., "IT infrastructure to support the secondary use of routinely acquired clinical imaging data for esearch," Neuroinformatics, vol. 13, No. 1, pp. 65-81, 2015,17 pages. (Year: 2015).*

Leung, K.Y. et al., "IT infrastructure to support the secondary use of routinely acquired clinical imaging data for research," Neuroinformatics, vol. 13, No. 1, pp. 65-81, 2015, 17 pages.

European Patent Office, "Extended European Search Report", issued in connection with application No. 17184452.5 dated Jan. 2, 2018, 8 pages.

United States Patent and Trademark Office, "Non-Final Office Action", issued in connection with U.S. Appl. No. 15/232,397 dated Nov. 16, 2018, 22 pages.

United States Patent and Trademark Office, "Notice of Allowance and Fee(s) Due", issued in connection with U.S. Appl. No. 15/232,397 dated Jun. 7, 2019, 9 pages.

Visceral, "Initial Report on Legal, Ethical, and Privacy Requirements for Data Distribution, Focusing on Competition 1", 2013, 10 pages.

Blender Stack Exchange, "Displaying Bounding Box Around Objects," 2013, 3 pages.

* cited by examiner

METHODS AND APPARATUS FOR RECORDING ANONYMIZED VOLUMETRIC DATA FROM MEDICAL IMAGE VISUALIZATION SOFTWARE

RELATED APPLICATION

This patent arises from a continuation of U.S. patent application Ser. No. 15/232,397, which was filed on Aug. 9, 2016. U.S. patent application Ser. No. 15/232,397 is hereby incorporated herein by reference in its entirety. Priority to U.S. patent application Ser. No. 15/232,397 is hereby claimed.

FIELD OF THE DISCLOSURE

This disclosure relates generally to volumetric data and, more particularly, to methods and apparatus for recording anonymized volumetric data from medial image visualization software.

BACKGROUND

Imaging devices (e.g., gamma camera, positron emission tomography (PET) scanner, computed tomography (CT) scanner, X-Ray machine, magnetic resonance imaging (MRI) machine, ultrasound scanner, etc.) generate medial images (e.g., native Digital Imaging and Communications in Medicine (DICOM) images) representative of the parts of the body (e.g., organs, tissues, etc.) to diagnose and/or treat diseases. Medical images may include volumetric data including voxels associated with the part of the body captured in the medical image. Medical image visualization software allows a clinician to segment, annotate, measure, and/or report functional or anatomical characteristics on various locations of a medical image. In some examples, a clinician may utilize the medical image visualization software to identify regions of interest with the medical image.

SUMMARY

Certain examples provide a method for recording anonymized volumetric data from medical image visualization software. The example method includes receiving a medical image. The example method further includes anonymizing the medical image outside of a region of interest by degrading the medical image outside a region corresponding to the region of interest and maintaining the resolution of the medical image inside the region corresponding to the region of interest. The example method further includes extracting data from the medical image. The example method further includes generating an archive based on the anonymized medical image and the data.

Certain examples provide an apparatus to record anonymized volumetric data from medical image visualization software. The example apparatus includes a receiver to receive a medical image. The example apparatus further includes an image anonymizer to anonymize the medical image outside of a region of interest by degrading medical image outside a region corresponding to the region of interest and maintaining the resolution of the medical image inside the region corresponding to the region of interest. The example apparatus further includes an extractor to extract data from the medical image. The example apparatus further includes an archive generator to generate an archive based on the anonymized medical image and the data.

Certain examples provide a computer readable medium comprising instructions which, when executed, cause a machine to record anonymized volumetric data from medical image visualization software. The example computer readable medium includes instructions that cause the machine to receive a medical image. The example computer readable medium includes instructions that cause the machine to anonymize the medical image outside of a region of interest by degrading the medical image outside a region corresponding to the region of interest and maintaining the resolution of the medical image inside the region corresponding to the region of interest. The example computer readable medium includes instructions that cause the machine to extract data from the medical image. The example computer readable medium includes instructions that cause the machine to generate an archive based on the anonymized medical image and the data.

BRIEF DESCRIPTION OF THE DRAWINGS

The figures are not to scale. Wherever possible, the same reference numbers will be used throughout the drawing(s) and accompanying written description to refer to the same or like parts.

DETAILED DESCRIPTION

Figure 1:
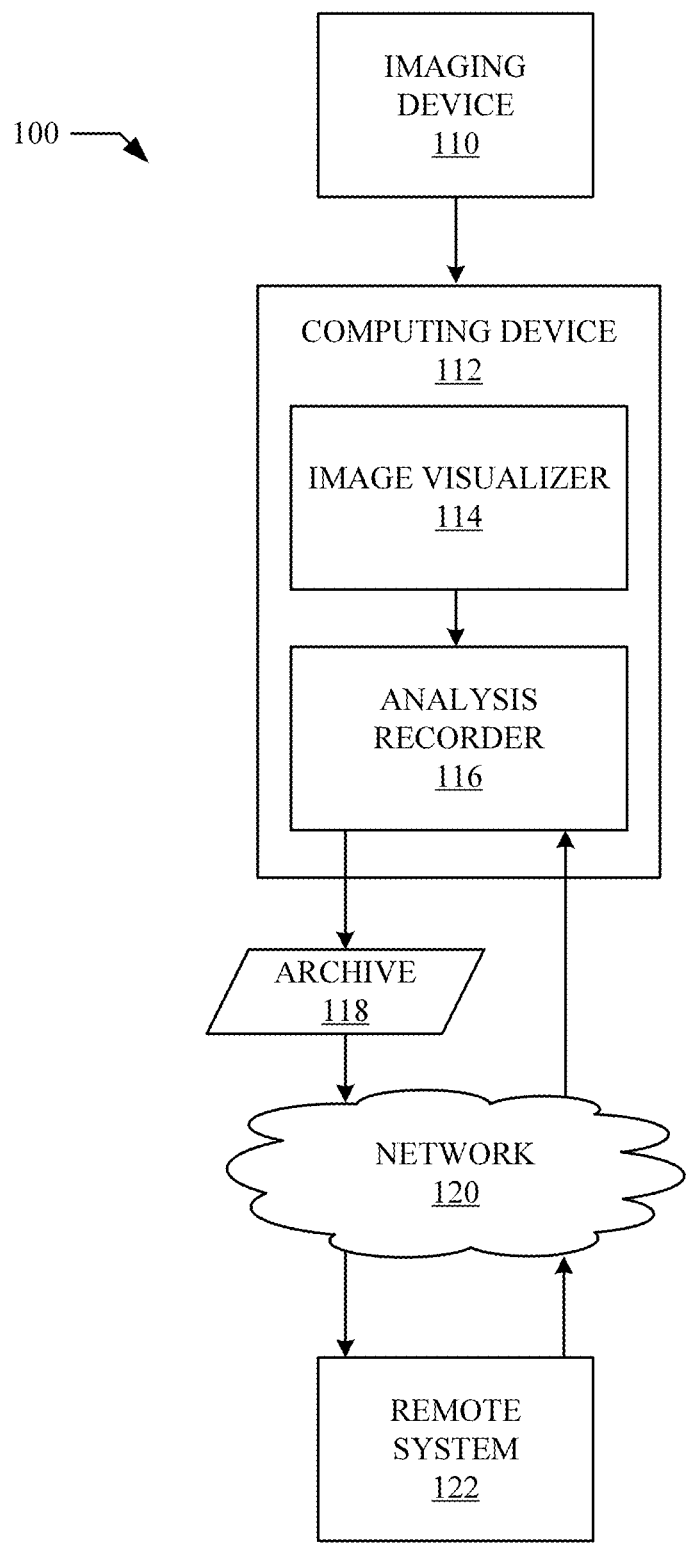
FIG. 1 is an illustration of an example analysis recorder to transmit archives including anonymized data representing regions of interest of a medical image.

Medical image visualization software allows clinicians to view medical images (e.g., native DICOM images) generated by medical imaging devices (e.g., gamma cameras, PET scanner, CT scanner, X-Ray machines, MRI etc.). In some examples, the medical images include pixel data (e.g., for two dimensional medical images) or voxel data (e.g., for three dimensional medical images) based on the dimensions of the part of the body the medical image represents. Such medical image visualization software helps clinicians to diagnosis and/or treat patients by analyzing regions of interest. Region of interests may be areas of the medical image that include an irregularity (e.g., lesion, tumor, stenosis, polyp, nodule, aneurysm, etc.). In some examples, medical image visualization software can track the evolution of a region of interest by viewing multiple images of the same patient at different points in time.

Medical image visualization software further allows a clinician to annotate and/or take notes on a medical image through the use of a user interface. The medical image visualization software saves the annotations, notes, and/or pixel/voxel data as part of the medical image for future analysis. The notes may include data related to prognosis, diagnosis, false negatives, false positives, etc. In some examples, the medical image visualization software embeds metadata into the saved medical images. Such metadata may include acquisition parameters, region of interest data, volumes geometry (e.g., size, dimensions, bit depth, etc.), a timestamp, patient identifiers, modality data, image data, image device data, location data, etc. As medical image visualization software and medical imaging devices improve, data corresponding to regions of interest improve and a database of annotated medical images may be desired to create a network of medical images to simplify and/or improve diagnosis using medical images of a plurality of patients from a plurality of locations. As used herein, annotated images are medical images that have been annotated by a clinician using medical image visualization software. Such annotations may include a segmentation of a region of interest and/or any other notes, edits, and/or comments made by the clinician. To build a remote database of annotated medical images from various locations (e.g., clinics) to provide a medical image network, patient confidentiality must be preserved. Additionally, because the file size of annotated medical images are large, it is desirable to reduce medical image file size in order to reduce the amount of data transmitted to a remote database and/or to conserve space in the remote database. Using examples disclosed herein, annotated medical images can be anonymously transferred to a remote system to generate a network of annotated medical images from various locations while preserving patient confidentiality. Additionally, by anonymizing the annotated medical images, examples disclosed herein reduce the file size associated with non-anonymized annotated medical images.

Examples disclosed herein include generating a compressed archive including an anonymized annotated medical image. Examples disclosed herein anonymize an annotated medical image by degrading (e.g., downsampling, encrypting, blurring, masking, etc.) the medical image in the region outside of the region of interest to provide low resolution image data outside the region of interest while maintaining a high resolution image within the region of interest segmented by a clinician. In some embodiments, examples disclosed herein generate a bounding box around the segmented region of interest, which may be bounded to preserve patient confidentiality. In such examples, examples disclosed herein anonymize the annotated medical image in the area outside of the bounding box while maintaining the high resolution within the bounding box. Because a high resolution medical image can be processed to identify a patient, downsampling and/or encrypting the medical image (e.g., to at least 5 mm in each direction) reduces the resolution of the image and/or the volumetric data (e.g., pixel value or voxel values) associated with the image to eliminate the possibility of identifying the patient. Degrading a medical image outside of a region of interest/bounding box, as opposed to a traditional method of cropping the region of interest, preserves position data relating to where the region of interest is located in relation to the rest of the organ and/or tissue being analyzed. Additionally, downsampling and/or encryption a medical image significantly reduces the size of the medical image.

The compressed archive disclosed herein further includes volumetric data associated with the medical image. Volumetric data include pixel values (e.g., associated with a two dimensional medical image) or voxel values (e.g., associated with a three dimensional medical image) corresponding the dimensions of the medical image. In some examples, the size of the pixels or the voxels is small corresponding to high resolution volumetric data (e.g., a list of voxel values within the region of interest/bounding box). In some examples, the size of the pixels or voxels is larger corresponding to low resolution volumetric data that cannot be used to identify a patient (e.g., a list of voxel values outside the region of interest/bounding box). To preserve patient confidentiality, examples disclosed herein generate an archive to include high resolution volumetric data for the region of interest/bounding box and low resolution volumetric data for the region outside of the region of interest/bounding box.

The compressed archive disclosed herein further includes anonymized metadata associated with the medical image. The anonymized metadata stored in associated with the medical image may include acquisition parameters, region of interest data, volumes geometry (e.g., size, dimensions, bit depth, etc.), a timestamp, non-identifiable patient signatures (e.g., encrypted patient data), modality data, image data, image device data, location data, etc. Examples disclosed herein remove any information that may be used to identify a patient from the metadata. The compressed archive disclosed herein further includes contextual data associated with the medical image. Contextual data includes any notes (e.g., notes generated by the clinician related to prognosis, diagnosis, etc.) and/or edits generated by a clinician using the medical image visualization software. Using examples disclosed herein, a compressed archive is generated and transmitted to a remote system to generate a network of medical images while preserving storage and patient confidentiality.

FIG. 1 illustrates an example image analysis and archiving system 100 including an analysis recorder 116 to transmit a local archive 118 generated by the analysis recorder 116 to a remote system 122. The illustration of FIG. 1 includes an imaging device 110, a computing device 112, an image visualizer 114, the analysis recorder 116, the local archive 118, a network 120, and the remote system 122.

The imaging device 110 of FIG. 1 is a medical imaging device that generates an image representative of a part of a body by scanning the part of the body part. In some examples, the imaging device 110 generates a three dimension image of a part of a body. In such examples, the imaging device 110 may scan a body part multiple times (e.g., multiple image slices) and combine the multiple images to generate the three dimensional image. The imaging device 110 may be an MRI scanner, an ultrasound scanner, an elastography scanner, a gamma camera, a PET scanner, a CT scanner, an X-Ray machine, and/or any other medical imaging device. The imaging device 110 transmits the generated medical image data to the computing device 112 for further processing (e.g., image reconstruction, post-processing, analytics, etc.).

The computing device 112 of FIG. 1 receives the medical images generated by the imaging device 110. The computing device 112 includes the image visualizer 114 and the analysis recorder 116. The image visualizer 114 may include a user interface to allow a user (e.g., a clinician) to view, segment, annotate, measure, and/or report functional and/or anatomical characteristics with respect to various locations of the received medical image. The image visualizer 114 prompts the clinician to identify and/or verify (e.g. segment) a region of interest within the medical image. The region of interest corresponds to the boundaries of an irregularity (e.g., lesion, tumor, stenosis, polyp, nodule, aneurysm, etc.). The image visualizer 114 incorporates segmentation data (e.g., data related to the region of interest), volumetric data (e.g., voxel values associated with the medical image), contextual data (e.g., user edits, inputs, clinician notes, etc.), and/or metadata into the medical image to generate an annotated image. Once a region of interest has been identified, the image visualizer 114 transmits the annotated image to the analysis recorder 116.

The analysis recorder 116 of FIG. 1 receives the annotated whole volume image from the image visualizer 114. The analysis recorder 116 generates the local archive 118 by extracting data (e.g., the volumetric data, the segmentation data, the contextual data, the metadata, etc.) from the annotated image. In some examples, the analysis recorder 116 receives extraction parameters from the remote system 122 to determine what information to extract from the annotated whole volume image and/or how to anonymize the annotated whole volume image in generating the local archive 118, as further described in conjunction with FIG. 2. Additionally, when the clinician has not identified a region of interest, the analysis recorder 116 may determine the region of interest based on the clinician notes and/or image analysis. In some examples, the analysis recorder 116 generates a bounding box that encloses the region of interest. The analysis recorder 116 anonymizes the local archive 118 by removing any identifying data in the extracted data and anonymize (e.g., downsample, encrypt, etc.) areas of the annotated whole volume image that are outside the region of interest/bounding box prior to generating the local archive 118. Because each patient has unique features, a patient may be identified based on a high resolution medical image displaying such unique features. Thus, anonymizing areas of the annotated image that are outside the region of interest/bounding box preserves a patient's identify by eliminating the possibility of identifying such unique features. In some examples, the analysis recorder 116 limits the size of the bounding box (e.g., to no more than 6 cm in each direction) to conserve patient confidentiality in images where the region of interest is sufficiently large enough to identify a patient. In some examples, the size of the bounding box may be based on what part of the body was imaged by the imaging device 110. For example, identifying a patient based on an image of a first region of the body (e.g. a section of the liver) may be very difficult; however, identifying the patient based on an image of a second region of the body (e.g., the face) may be very easy. In such an example, the dimensions of the bounding box for the first image may be much higher than the dimensions of the bounding box of the second image. Removing the identifying data preserves a patient's confidentiality by removing any data (e.g., name, date of birth, etc.) that may be used to identify the patient. The analysis recorder 116 may store locally generated archives in a file directory in the computing device 112. As further described in conjunction with FIG. 4, the analysis recorder 116 may perform a directory clean-up in order to conserve directory space. The analysis recorder 116 transmits the local archive 118 to the remote system 122 via the network 120. The analysis recorder 116 is further described in conjunction with FIG. 2.

The network 120 of FIG. 1 may be implemented using any type of public or private network such as, but not limited to, the Internet, a telephone network, a local area network (LAN), a cable network, and/or a wireless network. To enable communication via the network 120, the computing device 112 includes a communication interface that enables a connection to an Ethernet, a digital subscriber line (DSL), a telephone line, a coaxial cable, or any wireless connection, etc.

The remote system 122 of FIG. 1 receives the local archive 118 from the analysis recorder 116 via the network 120. The remote system 122 gathers local archives (e.g., including the local archive 118) from various computing devices (e.g., including the computing device 112) to generate a database of remote medical image archives. In some examples, the remote system 122 includes a machine learning algorithm to analyze, correlate, and/or process anonymized archives to develop large data analytics based on archives from various clinical sites based. For example, a plurality of anonymized images can be gathered by the remote system 122 to train and test a neural network to be deployed to automatically detect regions of interest in images (e.g., autocontour, etc.). In some examples, the remote system 122 transmits extraction parameters to optimize the local archive 118. For example, the remote system 122 may require additional data or determine that some of the data of the local archive 118 is unnecessary. In such an example, the remote system 122 may include extraction parameters to instruct the analysis recorder 116 to generate the local archive 118 based on the identified extraction parameters.

Figure 2:
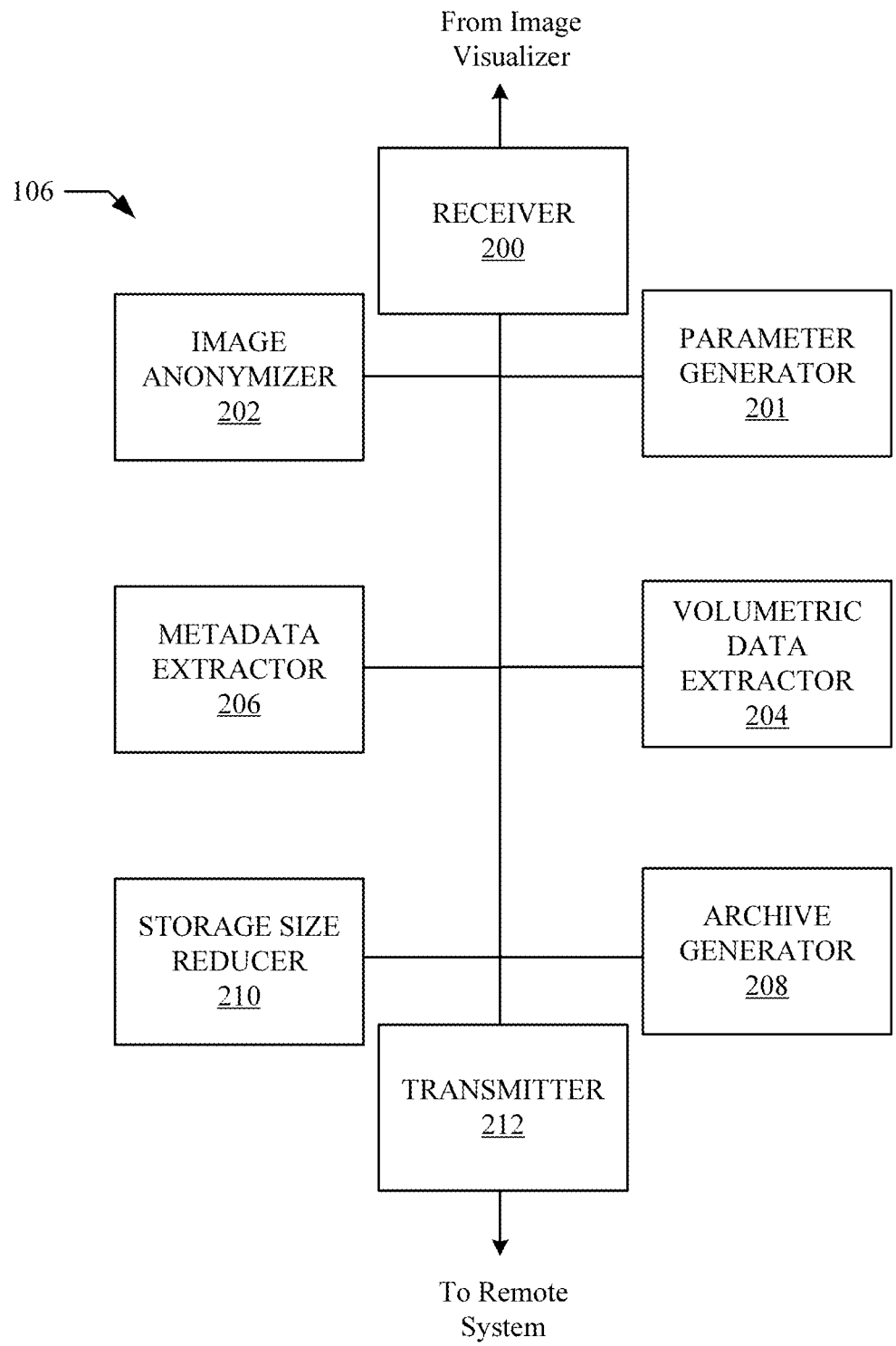
FIG. 2 is an illustration of the example analysis recorder used to transmit the archives to an example remote system of FIG. 1.

FIG. 2 is a block diagram of an example implementation for the analysis recorder 116 of FIG. 1. The analysis recorder 116 of the example of FIG. 2 is structured to generate anonymized archives (e.g., including the local archive 118 of FIG. 1) based on received annotated images and transmit the archives to the remote system 122 of FIG. 1. The analysis recorder 116 of FIG. 2 includes a receiver 200, a parameter generator 201, an image anonymizer 202, a volumetric data extractor 204, a metadata extractor 206, an archive generator 208, a storage size reducer 210, and a transmitter 212.

The receiver 200 of FIG. 2 receives annotated images from the image visualizer 114 of FIG. 1. As described above in conjunction with FIG. 1, the annotated images include a high resolution medical image with a segmented region of interest identified by a user. The annotated image further includes volumetric data, segmentation data, contextual data, and metadata. In some examples, the receiver 200 receives extraction parameters from the remote system 122 to customize the generated local archive 118 of FIG. 1.

The parameter generator 201 of FIG. 2 generates the extraction parameters corresponding to the generation of the local archive 118. The extraction parameters include how to anonymize an annotated image and what metadata, volumetric data, and/or contextual data to extract from the annotated image to generate the local archive 118. The extraction parameters may include the resolution of the anonymized region, a maximum size of the region of interest, what metadata to extract from the annotated image, the resolution of the volumetric data, what contextual data to extract from the annotated image, etc. The extraction parameters may be determined based on image capture parameters and/or instructions from the remote system 122. Additionally, the parameter generator 201 may determine a region of interest when the clinician has not identified the region of interest. The parameter generator 201 may determine the region of interest based on the location of the clinician notes (e.g., a location identified in a clinician note and/or the actual location of a note that is placed on the image, etc.) and/or a comparison of the image (which includes an irregularity) to a reference image (without an irregularity). In some examples, the parameter generator 201 may interface with the clinician to verify that the determined region of interest is the correct region of interest.

The image anonymizer 202 of FIG. 2 anonymizes the annotated whole volume image in the region outside of the region of interest by degrading part of the annotated whole volume image. In some examples, the image anonymizer 202 generates a bounding box that encompasses the region of interest. In such examples, the image anonymizer 202 may limit the size (e.g., to 6 mm in every direction, etc.) of the bounding box to preserve patient confidentiality. In some examples, the size of the bounding box may be based on what part of the body was imaged by the imaging device 110. For example, identifying a patient based on an image of a first region of the body (e.g. a section of the liver) may be very difficult; however, identifying the patient based on an image of a second region of the body (e.g., the face) may be very easy. In such an example, the dimensions of the bounding box for the first image may be much higher than the dimensions of the bounding box of the second image.

In some examples, the image anonymizer 202 of FIG. 2 anonymizes the whole volume image by downsampling the voxels in the whole volume image outside the region of interest so that the whole volume voxel size is increase to a minimum voxel volume. For example, the image anonymizer 202 may downsample the whole volume voxel size from 1 mm in each direction (e.g. a voxel volume of 1 mm$^3$) to at least 5 mm in each direction (e.g., a voxel volume of 5 mm$^3$). In such an example, the image anonymizer 202 maintains the voxel volume of 1 mm$^3$ in the region of interest/bounding box. Increasing a whole volume voxel size to a minimum volume decreases the resolution (e.g., blurs) of the annotated whole volume image such that the patient cannot be identified by the downsized whole volume image. The voxel volume may be based on the extraction parameters. Downsampling and/or blurring the whole volume image is a destructive process (e.g., the original whole volume image cannot be recovered once downsampled) that guaranties de-identification. Alternatively, the image anonymizer 202 may anonymize the whole volume image by degrading the whole volume image using any other degrading techniques. In some examples, the image anonymizer 202 may blur and compress the region outside the region of interest. In some examples, the anonymizer 202 may filter the region outside the region of interest to mask structures that can be used to identify a patient (e.g., such as a face). In some examples, the anonymizer 202 may match the whole volume to a generic template/model. In such examples, the anonymizer 202 will maintain the image in the region of interest and/or bounding box and replace the region outside the region of interest and/or bounding box with the template image/model.

In some examples, the image anonymizer 202 of FIG. 2 may apply an encryption to the voxels in the whole volume image outside the region of interest to increase the minimum voxel volume. In such examples, the image anonymizer 202 may generate an encryption key to decrypt the encrypted whole volume image. Because the encryption key can decrypt the encrypted whole volume image, encryption is not a destructive process. Thus, techniques for private key generation may be necessary to guarantee de-identification. Decrypting the encrypted whole volume image allows a user in possession of the encryption key to, at a point after the whole volume image is encrypted (e.g., blurred to a lower resolution), regenerate the whole volume image at a high resolution. An example of 1) an annotated whole volume image in high resolution and 2) an annotated whole volume image in high resolution inside a region of interest and low resolution outside of the region of interest are illustrated and further described in conjunction with FIG. 7.

The volumetric data extractor 204 of FIG. 2 extracts volumetric data associated with the segmented region of interest. The volumetric data includes the voxel values within the region of interest. The volumetric data identifies the dimensions of the region of interest (e.g., the volume of the region of interest). In some examples, the volumetric data extractor 204 generates a compact representation of the whole volume region outside of the region of interest. Because the compact representation has a lower resolution, the whole volume region outside of the region of interest is anonymized. For example, the volumetric data extractor 204 may include compact voxel values representative of a group of voxels based on the anonymized region. In such an example, each compact value may represent a large group of voxels within a voxel volume (e.g., all voxels within a 5 mm$^3$ area of the whole volume image). The compact value may be based on the extraction parameters. As described above, the low resolution compact voxel values cannot be used to identify the patient.

The metadata extractor 206 of FIG. 2 extracts metadata from the annotated whole volume image. The metadata may include acquisition parameters, region of interest data, volumes geometry (e.g., size, dimensions, bit depth, etc.), a timestamp, patient identifiers, modality data, image data, image device data, location data, etc. The type of metadata extracted from the annotated whole volume image may be based on the extraction parameters. The metadata extractor 206 removes any data that may be used to identify a patient to anonymize the metadata. In some examples, the metadata extractor 206 may replace a patient identifier with an anonymized identifier to identify that the whole volume image came from a particular patient without revealing the identity of the patient. Generating an anonymized identifier may allow the local archive 118 to include multiple whole volume images from the same patient at various points in time to track the evolution of the region of interest as a function of time. Additionally or alternatively, the anonymized identifier may be used by the remote system 122 (FIG. 1) to track the evolution of the region of interest as a function of time. In some examples, the metadata extractor 206 and the volumetric data extractor 204 may be combined into one extractor.

The archive generator 208 of FIG. 2 generates an archive (e.g., the local archive 118 of FIG. 1) based on the volumetric data extracted by the volumetric data extractor 204, the anonymized metadata extracted by the metadata extractor 206, contextual data extracted by the archive generator 208, and/or the anonymized whole volume image from the image anonymizer 202. In some examples, the archive generator 208 generates the local archive 118 by generating multiple files to represent an annotated whole volume image. For example, the local archive 118 may include a file for the segmentation of the region of interest (e.g., the high resolution region of interest volume image), a file for the voxel values of the region of interest, a file for the anonymized area outside the region of interest (e.g., the low resolution whole volume image), a file for the anonymized metadata, a file for the acquisition parameters, and a file for the clinician edits and/or notes. The archive generator 208 may compress the multiple files into a single file (e.g., the local archive 118) using any type of compression technique (e.g., tar, bz2, 7z, rar, zip, etc.). The archive generator 208 stores the local archive 118 in a directory within the computing device 112 (FIG. 1). In some examples, the archive generator 208 may update the local archive 118 to include additional data associated with an additional annotated whole volume image with an identifier matching an identifier associated with a previously generated archive.

The storage size reducer 210 of FIG. 2 performs a directory clean-up based on the available space in the directory where the archives are stored. After an archive is generated, the storage size reducer 210 determines if the available directory space is below a space threshold. When the available directory space is below the space threshold, the storage size reducer 210 deletes the oldest stored archive to increase the available directory space (e.g., satisfy the space threshold). In some examples, the storage size reducer 210 determines if the oldest stored archive has been transmitted to the remote system 122 prior to deletion to ensure that the archive is transmitted prior to deletion.

The transmitter 212 of FIG. 2 transmits the local archive 118 to the remote system 122 via the network 120 (FIG. 1). In some examples, the transmitter 212 transmits the local archive 118 as soon as the archive is generated. In some examples, the transmitter 212 transmits the local archive 118 based on a set schedule (e.g., daily, weekly, monthly, etc.). In some examples the transmitter 212 transmits the local archive 118 prior to deletion during a direction clean-up operation.

While example manners of implementing the example unique audience analysis recorder 116 of FIG. 1 are illustrated in conjunction with FIG. 2, elements, processes and/or devices illustrated in conjunction with FIG. 2 may be combined, divided, re-arranged, omitted, eliminated and/or implemented in any other way. Further, the receiver 200, the parameter generator 201, the image anonymizer 202, the volumetric data extractor 204, the metadata extractor 206, the archive generator 208, the storage size reducer 210, the transmitter 212, and/or, more generally, the analysis recorder 116 of FIG. 2 may be implemented by hardware, machine readable instructions, software, firmware and/or any combination of hardware, machine readable instructions, software and/or firmware. Thus, for example, any of the receiver 200, the parameter generator 201, the image anonymizer 202, the volumetric data extractor 204, the metadata extractor 206, the archive generator 208, the storage size reducer 210, the transmitter 212, and/or, more generally, the analysis recorder 116 of FIG. 2 can be implemented by analog and/or digital circuit(s), logic circuit(s), programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the receiver 200, the parameter generator 201, the image anonymizer 202, the volumetric data extractor 204, the metadata extractor 206, the archive generator 208, the storage size reducer 210, the transmitter 212, and/or, more generally, the analysis recorder 116 of FIG. 2 is/are hereby expressly defined to include a tangible computer readable storage device or storage disk such as a memory, a digital versatile disk (DVD), a compact disk (CD), a Blu-ray disk, etc. storing the software and/or firmware. Further still, the analysis recorder 116 of FIG. 2 include elements, processes and/or devices in addition to, or instead of, those illustrated in conjunction with FIGS. 3 and 4, and/or may include more than one of any or all of the illustrated elements, processes and devices.

Figure 3:
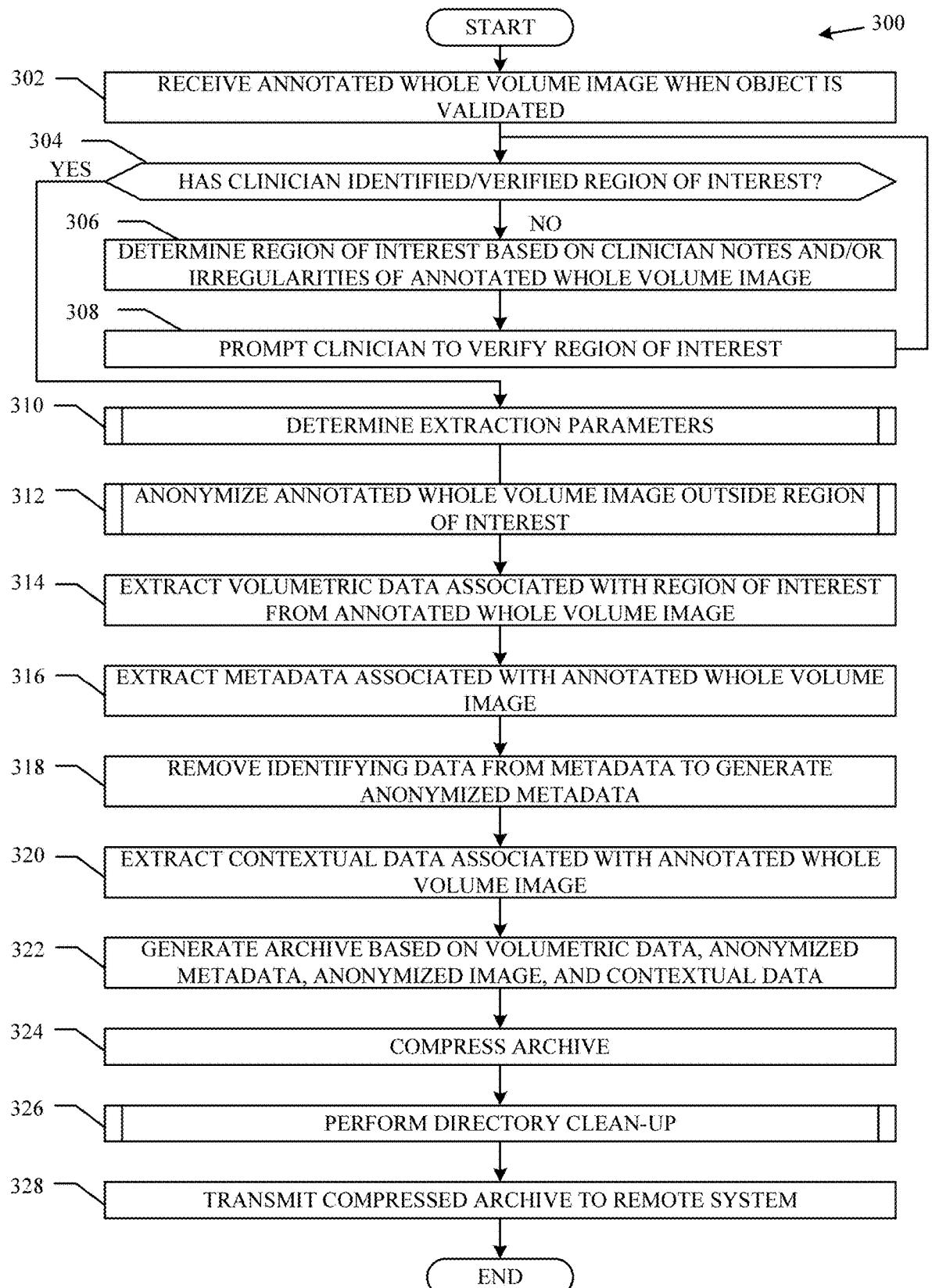
FIG. 3 is a flowchart representative of example machine readable instructions that may be executed to implement the example analysis recorder of FIG. 2 to determine generate and transmit the archives of FIG. 1.
Figure 4:
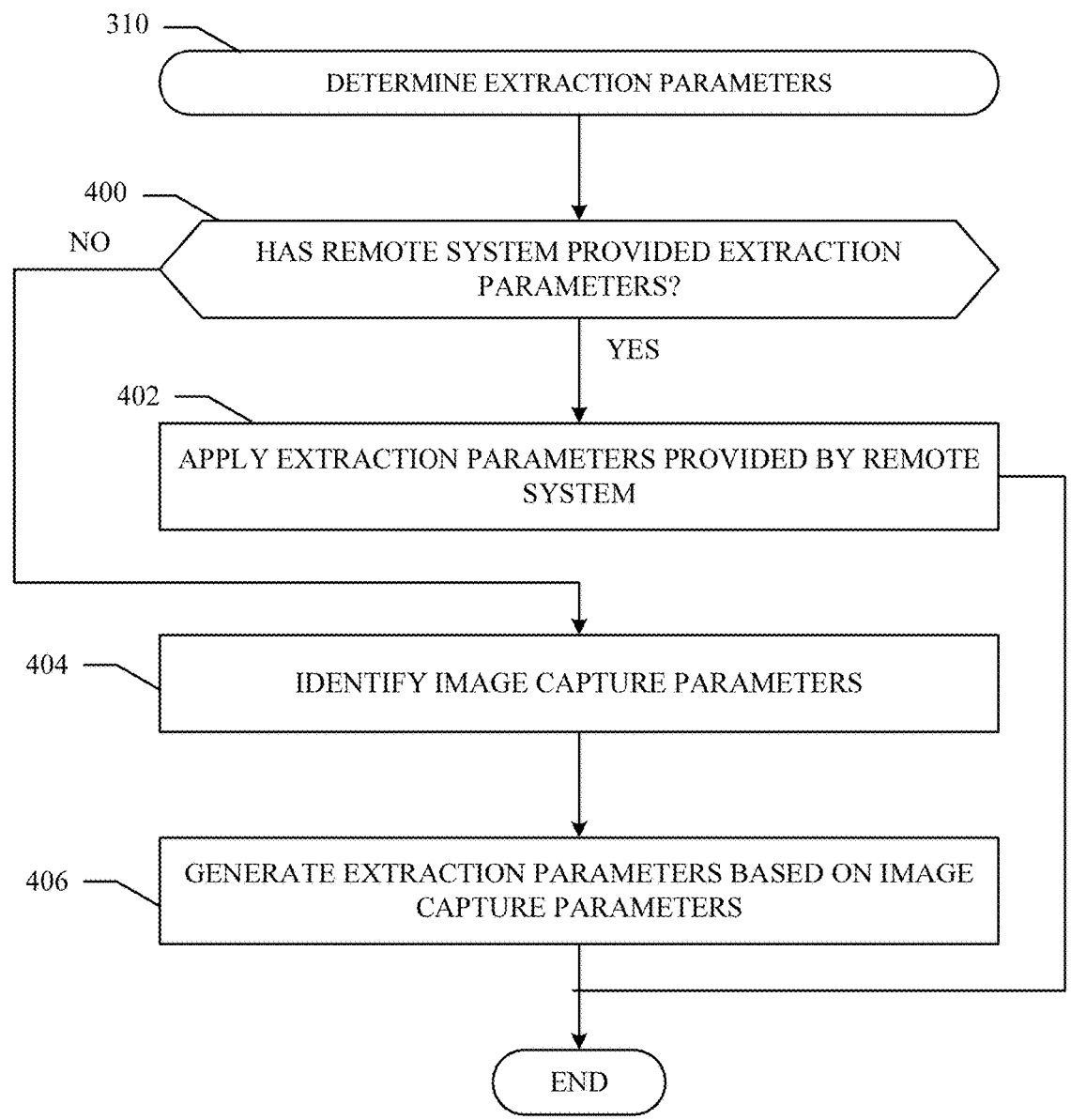
FIG. 4 is a flowchart representative of example machine readable instructions that may be executed to implement the example analysis recorder of FIG. 2 to determine extraction parameters and a region of interest.

Flowcharts representative of example machine readable instructions for implementing the analysis recorder 116 of FIG. 2 are shown in conjunction with FIGS. 3 and 4. In the examples, the machine readable instructions include a program for execution by a processor such as the processor 812 shown in the example processor platform 800 discussed below in connection with FIG. 8. The program may be embodied in machine readable instructions stored on a tangible computer readable storage medium such as a CD-ROM, a floppy disk, a hard drive, a digital versatile disk (DVD), a Blu-ray disk, or a memory associated with the processor 812, but the entire program and/or parts thereof could alternatively be executed by a device other than the processor 812 and/or embodied in firmware or dedicated hardware. Further, although the example program is described with reference to the flowcharts illustrated in conjunction with FIGS. 3 and 4, many other methods of implementing the analysis recorder 116 of FIG. 2 may alternatively be used. For example, the order of execution of the blocks may be changed, and/or some of the blocks described may be changed, eliminated, or combined. Although the flowcharts of FIGS. 3 and 4 depict example operations in an illustrated order, these operations are not exhaustive and are not limited to the illustrated order. In addition, various changes and modifications may be made by one skilled in the art within the spirit and scope of the disclosure. For example, blocks illustrated in the flowchart may be performed in an alternative order or may be performed in parallel.

As mentioned above, the example processes of FIGS. 3 and 4 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example processes of FIGS. 3 and 4 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended. In addition, the term "including" is open-ended in the same manner as the term "comprising" is open-ended.

FIG. 3 is a flowchart 300 representative of example machine readable instructions that may be executed by the analysis recorder 116 of FIG. 2 to generate the local archive 118 of FIG. 1. Although the instructions of FIG. 3 are described in conjunction with the analysis recorder 116 of FIG. 2, the example instructions may be utilized by any type of analysis recorder.

At block 302, the receiver 200 receives an annotated whole volume image from the image visualizer 114 when an object, such as a lesion, is validated in the image. In some examples, the validation occurs when the clinician accepts the segmentation, edits, notes, etc., with respect to the object using the image visualizer 114. Once the clinician accepts, the image visualizer 114 transmits the annotated whole volume image to the receiver 200 of the analysis recorder 116. As described above in conjunction with FIG. 1, the annotated whole volume image is an image of part of the body (e.g., an organ, tissue, etc.) generated by the imaging device 110 of FIG. 1. The annotated whole volume image may be a three dimensional image including voxel values associated with the image. Additionally, the annotated whole volume image may include a region of interest segmented by a clinician and/or edits or notes generated by the clinician.

At block 304, the parameter generator 201 determines if the clinician has identified/verified a region of interest in the annotated whole volume image. If the parameter generator 201 determines that the clinician has identified a region of interest in the annotated whole volume image, the process continues to block 310 of FIG. 3 based on the identified region of interest. If the parameter generator 201 determines that the clinician has not identified a region of interest in the annotated whole volume image, then the parameter generator 201 automatically determines the region of interest based on clinician notes (e.g., the location of the clinician notes on the annotated whole volume image or a location determined based on the clinician notes, etc.) and/or irregularities of the annotated whole volume image (block 306). For example, if the clinician generated notes within a region of the annotated whole volume image, the parameter generator 201 may determine that the region associated with the clinician notes is the region of interest.

Additionally or alternatively, the parameter generator 201 may compare the annotated whole volume image to a reference (e.g., truth) image. The reference image is an image illustrating the same body part as the annotated whole volume image; however, the reference image does not include an irregularity (e.g., is a "gold standard" or library image used for comparison an anomaly identification, etc.). The parameter generator 201 may determine the region of interest based on a mismatch between the annotated whole volume image and the reference image, for example. In some examples, the parameter generator 201 may interface with the clinician to verify that the determined region of interest is the correct region of interest.

At block 308, the transmitter 212 transmits instructions to a user interface of the computing device 112 (FIG. 1) to prompt the clinician to verify the region of interest. In some examples, if the clinician verifies the region of interest, the parameter generator 201 may store the parameters used to verify the region of interest to improve a local computer learning algorithm to determine regions of interest. In such examples, the archive generator 208 may include the parameters to improve a remote computer learning algorithm corresponding to the remote system 122 of FIG. 1.

At block 310, the parameter generator 201 determines extraction parameters and a region of interest for the annotated whole volume image, as further described in conjunction with FIG. 4. At block 312, the image anonymizer 202 anonymizes the annotated whole volume image outside the region of interest and/or a bounding box around the region of interest. The image anonymizer 202 may anonymize the annotated whole volume image by encrypting and/or down-sampling voxels into voxel groups to create a low resolution representation of the whole volume image outside the region of interest, as further described in conjunction with FIG. 5. As described above, a low resolution whole volume image cannot be used to identify a user (e.g., a low resolution whole volume image is anonymized).

At block 314, the volumetric data extractor 204 extracts volumetric data associated with the region of interest/bounding box from the annotated whole volume image. The volumetric data includes voxel values within the region of interest/bounding box (e.g., high resolution voxel values) and a compact representation of voxel values outside the region of interest/bounding box (e.g., low resolution voxel values). At block 316, the metadata extractor 206 extracts metadata associated with the annotated whole volume image. The metadata includes acquisition parameters, region of interest data, volumes geometry (e.g., size, dimensions, bit depth, etc.), a timestamp, patient identifiers, modality data, image data, image device data, location data, etc.

At block 318, the metadata extractor 206 removes any identifying data from the extracted metadata to generate anonymized metadata. In some examples, as described above in conjunction with FIG. 2, the metadata extractor 206 replaces the identifying data with an anonymized identifier to correspond the annotated whole volume image with other annotated whole volume images associated with the same patient without revealing the identity of the patient. At block 320, the archive generator 208 extracts any contextual data associated with the annotated whole volume image such as clinician edits and/or notes.

At block 322, the archive generator 208 generates the local archive 118 based on the volumetric data (e.g., including both the voxel values inside the segmented region of interest/bounding box), the anonymized metadata (e.g., acquisition parameters, region of interest information, volume geometry, etc.), the anonymized image (e.g., the segmentation region of interest in high resolution and the low resolution image outside of the region of interest and/or an indication of a high resolution portion and/or a low resolution portion of the whole volume annotated image), and/or contextual data (e.g., clinician notes, edits, etc.). As described above in conjunction with FIG. 2, the archive generator 208 may generate multiple files for the different data and compress the files into a single archive (e.g., the local archive 118 of FIG. 1). In some examples, the archive generator 208 may determine that the annotated whole volume image is associated with a second stored archive based on a matching anonymized identifier. In such examples, the archive generator 208 may update the second archive to include the volumetric data, the anonymized metadata, the anonymized image, and/or contextual data associated with the annotated whole volume image to provide an evolution of the region of interest as a function of time.

At block 324, the archive generator 208 compresses the local archive 118 to reduce the size of the archive. Reducing the size of the local archive 118 reduces the amount of data being transmitted by the transmitter 212 (e.g., increasing efficiency of the analysis recorder 116) and allows the transmitter 212 to transmit the local archive 118 to the remote system 122 even when the network 120 has limited bandwidth. At block 326, the storage size reducer 210 performs a directory clean-up to reduce the amount of data stored in the computing device 112 (FIG. 1), as further described in conjunction with FIG. 6. At block 328, the transmitter 212 transmits the compressed archive to the remote system 122 of FIG. 1.

FIG. 4 is a flowchart 310 representative of example machine readable instructions that may be executed by the analysis recorder 116 of FIG. 2 to determine extraction parameters to generate the local archive 118 of FIG. 1, as shown in block 310 of FIG. 3. Although the instructions of FIG. 4 are described in conjunction with the analysis recorder 116 of FIG. 2, the example instructions may be utilized by any type of analysis recorder.

At block 400, the parameter generator 201 (FIG. 2) determines if the remote system 122 has provided extraction parameters to the receiver 200 of FIG. 2. As described above in conjunction with FIG. 1, the remote system 122 may transmit extraction parameters to adjust the anonymization and/or extraction of information from the annotated whole volume image. For example, the extraction parameters may include data related to the resolution (e.g., voxel volume) of the downsampling and/or encryption. If the parameter generator 201 determines that the remote system 122 has provided extraction parameters, the parameter generator 201 applies the extraction parameters provided by the remote system 122 to generate the local archive 118 (block 402).

If the parameter generator 201 determines that the remote system 122 has not provided extraction parameters, the parameter generator 201 identifies the image capture parameters (block 404). The optimal extraction parameters may be different for different annotated whole volume images based on the image capture parameters (e.g., the resolution of the annotated whole volume image, the body part imaged in the annotated whole volume image, the size of the annotated whole volume image, the device data corresponding to the image device 110, etc.). For example, a first image of a first body part may identify a patient easier than a second image of a second body part. In such an example, the resolution associated with anonymizing of the first image may need to be lower than the resolution associated with the anonymizing of the second image to preserve patient confidentiality. At block 406, the parameter generator 201 generates the extraction parameters based on the image capture parameters.

Figure 5:
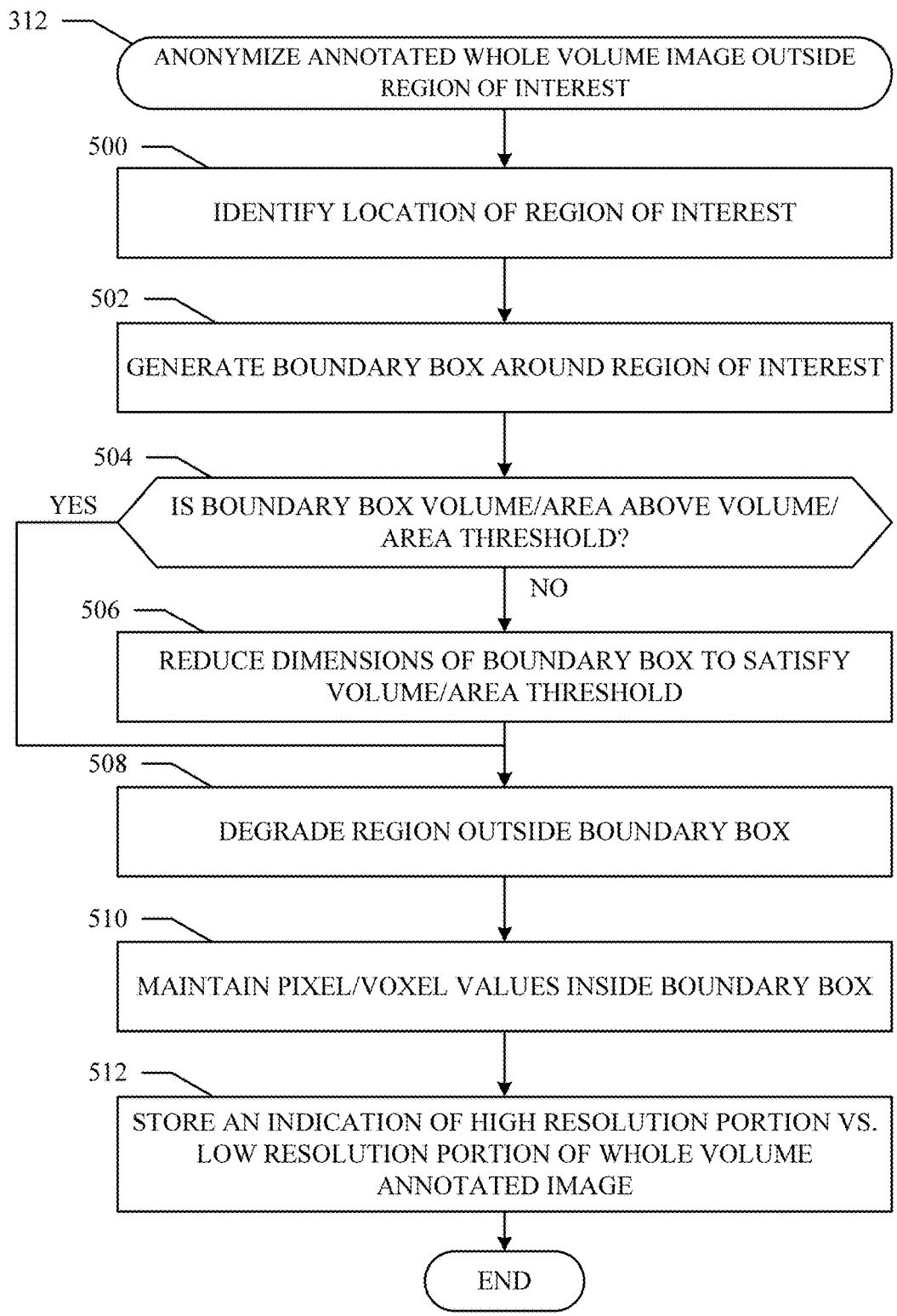
FIG. 5 is a flowchart representative of example machine readable instructions that may be executed to implement the example analysis recorder of FIG. 2 to anonymize an annotated whole volume image outside a region of interest.

FIG. 5 is a flowchart 312 representative of example machine readable instructions that may be executed by the analysis recorder 116 of FIG. 2 to anonymize an annotated whole volume image outside a region of interest using a bounding box, as shown in block 312 of FIG. 3. Although the instructions of FIG. 5 are described in conjunction with the analysis recorder 116 of FIG. 2, the example instructions may be utilized by any type of analysis recorder.

At block 500, the image anonymizer 202 identifies the location of a region of interest of the annotated whole volume image. As described above, the region of interest includes an area of the annotated whole volume image that has been segmented by the clinician. The region of interest may be identified directly by the clinician or may be determined by the analysis recorder 116 and verified by the clinician. At block 502, the image anonymizer 202 generates a bounding box around the region of interest. The bounding box may be two-dimensional, for two-dimensional medical images, or three-dimensional, for three-dimensional medical images. The bounding box is generated so that the entire region of interest is included in the bounding box. In some examples, the bounding box may be generated with a buffer (e.g., 1 mm, etc.) so that no edge of the region of interest is within the buffer of the bounding box.

At block 504, the image anonymizer 202 determines if the bounding box volume (e.g., for three-dimensional images) or area (e.g., for two-dimensional images) is above a volume/area threshold. As described above, because the volumetric data and image quality within the bounding box be in a high resolution, a bounding box that is too large (e.g., above a threshold) may be used to identify a patient. Alternatively, the image anonymizer 202 may determine if the bounding box dimensions satisfy a dimension threshold. For example, the dimension threshold may be limited to 6 cm in every direction. In such an example, if the bounding box size is more than 6 cm in any direction, the image anonymizer 202 determines that the dimensions of the bounding box do not satisfy the dimension threshold. In some examples, the size of the bounding box may be based on what part of the body was imaged by the imaging device 110. For example, identifying a patient based on an image of a first region of the body (e.g. a section of the liver) may be very difficult; however, identifying the patient based on an image of a second region of the body (e.g., the face) may be very easy. In such an example, the dimensions of the threshold for the first image may be much higher than the dimensions of the threshold of the second image.

If the volume/area of the generated bounding box does not satisfy the volume/area threshold (or dimension threshold), then, at block 506, the image anonymizer 202 reduces the dimensions of the bounding box to satisfy the volume/area threshold. In some examples, the image anonymizer 202 reduces the buffer to satisfy the threshold.

At block 508, the image anonymizer 202 degrades the region outside the boundary box. As described above in conjunction with FIG. 2, degrading the annotated whole volume image may include downsampling/encrypting the pixel/voxel values reduces the resolution of the whole volume annotated image to preserve patient confidentiality. For example, the image anonymizer 202 may downsample voxel value from a voxel size of 1 mm in each direction (e.g., high resolution) to a voxel size of 5 mm in each direction (e.g., low resolution). Alternatively, the image anonymizer 202 may blur and compress the region outside the region of interest, filter the region outside the region of interest (e.g., to mask identifying structures), or match the region outside the region of interest with a template/model image.

At block 510, the image anonymizer 202 maintains the pixel/voxel values inside the bounding box to maintain a high resolution image within the bounding box. As described above in conjunction with FIG. 2, the high resolution image is maintained to allow the region of interest to be analyzed/processed by the remote system 122 of FIG. 1.

At block 512, the image anonymizer 202 stores an indication of the high resolution portion of the annotated whole volume image to a low resolution portion of the annotated whole volume image. The indication corresponds to the size of the region of interest compared to the region of the body represented in the annotated whole volume image. The indication may be used to track the evolution of a region of interest by viewing multiple images of the same patient at different points in time.

Figure 6:
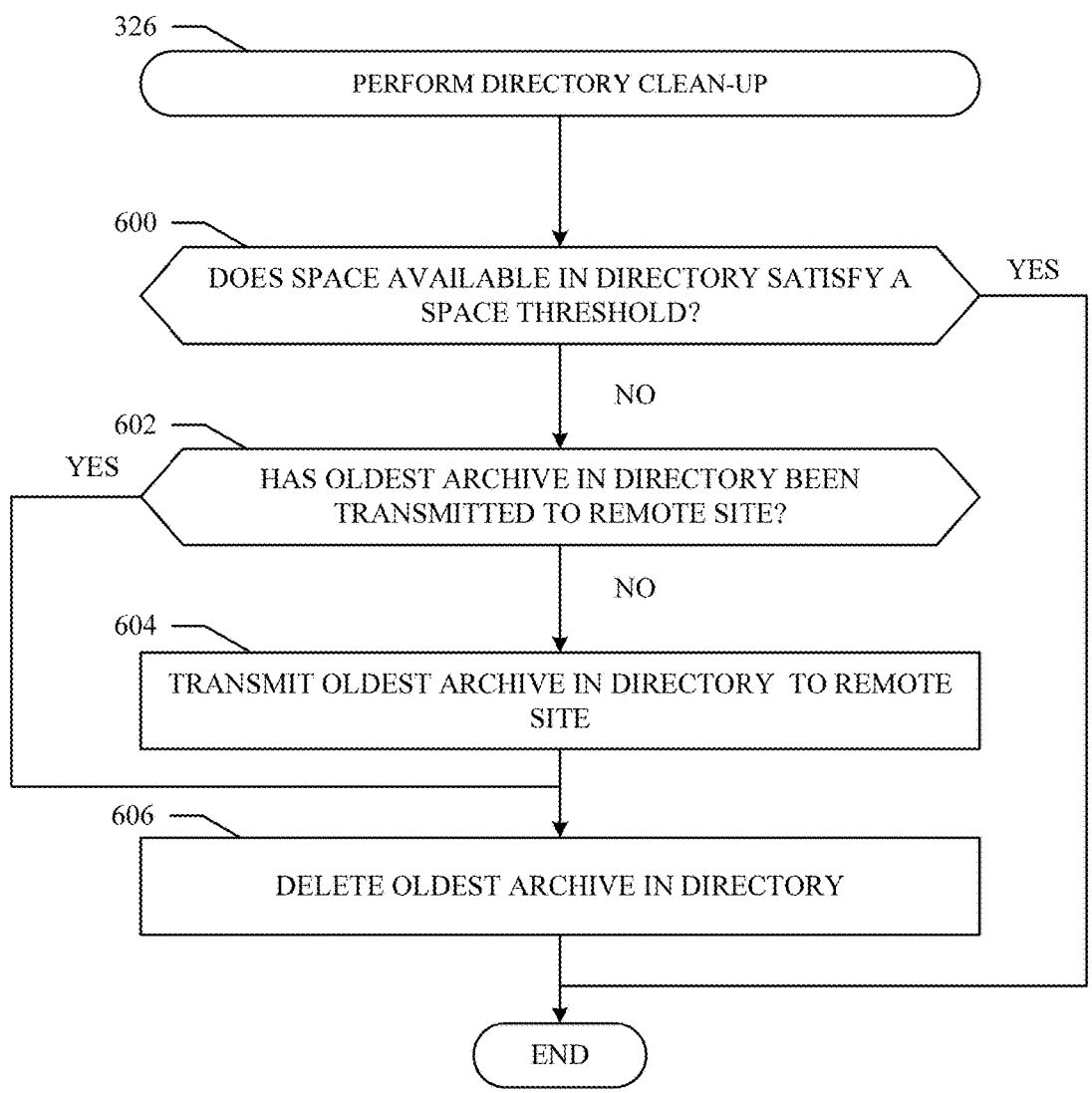
FIG. 6 is a flowchart representative of example machine readable instructions that may be executed to implement the example analysis recorder of FIG. 2 to perform a directory clean-up.

FIG. 6 is a flowchart 326 representative of example machine readable instructions that may be executed by the analysis recorder 116 of FIG. 2 to perform a directory clean-up, as shown in block 326 of FIG. 3. Although the instructions of FIG. 6 are described in conjunction with the analysis recorder 116 of FIG. 2, the example instructions may be utilized by any type of analysis recorder.

At block 600, the storage size reducer 210 determines if the space available in the directory where the archives are stored satisfies a space threshold. As described above in conjunction with FIG. 2, the available directory space may be limited. Thus, when the available space is below a minimum space threshold, generating additional archives will cause saturation to the computing device 112 (FIG. 1). If the storage size reducer 210 determines that the available directory space satisfies the space threshold (e.g., the available directory space is above the minimum space threshold), the storage size reducer 210 determines that a directory clean-up is unnecessary and the process ends.

If the storage size reducer 210 determines that the available directory space does not satisfy the space threshold, then, at block 602, the storage size reducer 210 determines whether the oldest archive (e.g., the archive in the directory with the oldest creation date) has been transmitted to the remote system 122 of FIG. 1. If the storage size reducer 210 determines that the oldest archive has not been transmitted to the remote system 122, then, at block 604, the storage size reducer 210 instructs the transmitter 212 to transmit the oldest archive in the director to the remote system 122. At block 606, the storage size reducer 210 deletes the oldest archive in the directory to prevent directory saturation.

Although the flowchart 326 is described based on a single oldest archive, the storage size reducer 210 may delete a group of oldest archives in a directory based on the available directory space and/or the space threshold. For example, if the oldest archive is 500 kilobytes (Kb) and the available space is 1 megabyte (Mb) lower than the space threshold, then the storage size reducer 210 determines that deleting the oldest archive does not clear up enough space to satisfy the minimum space threshold. In such an example, the storage size reducer 210 may determine how many of the oldest archives to delete to satisfy the minimum space threshold after the deletion and delete the group of oldest archives. If any of the oldest archives have not been transmitted to the remote system 122, the storage size reducer 210 may transmit those archives to the remote system 122 prior to deletion.

Figure 7:
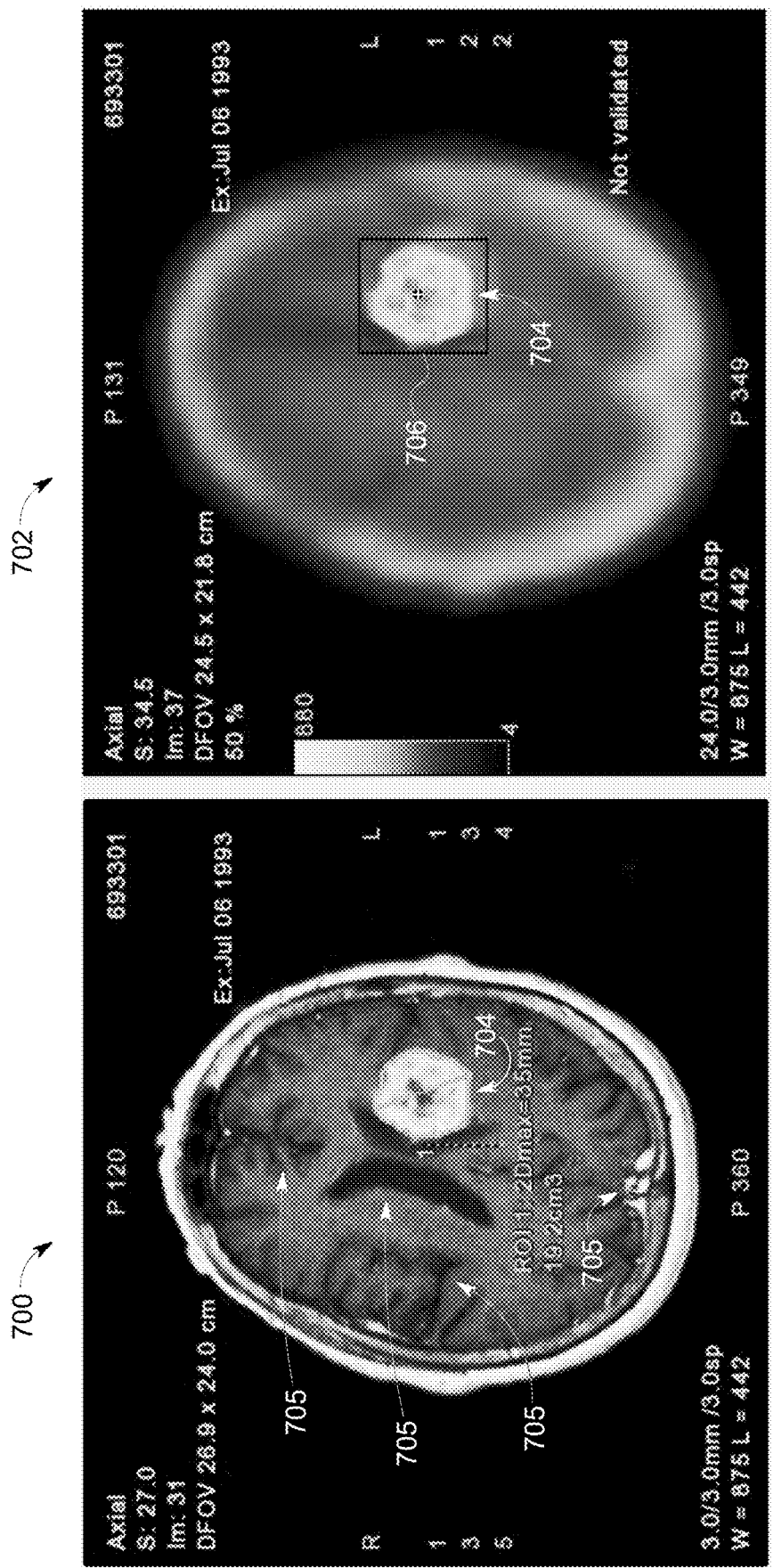
FIG. 7 illustrates an example annotated image and the example annotated image after being anonymized by the example analysis recorder of FIGS. 1 and 2.

FIG. 7 illustrates an annotated whole volume image 700 and an anonymized image 702. The anonymized image 702 is the annotated whole volume image 700 after being anonymized by the image anonymizer 202 of FIG. 2. Both the annotated whole volume image 700 and the anonymized image 702 include a region of interest 704 which is segmented by a clinician. The whole volume image 700 includes features 705 displayed in high resolution. The anonymized image 702 includes a bounding box 706 defining a high resolution portion of the image.

The annotated whole volume image 700 of FIG. 7 is a high resolution image from the imaging device 110 (FIG. 1) illustrating a brain with a lesion (e.g., a tumor). The annotated whole volume image 700 has been analyzed by a clinician using the image visualizer 114 (FIG. 1) to segment, make edits and/or notes (e.g., contextual data), and identify the region of interest 704. As described above, the annotated whole volume image 700 may include voxel value (e.g., volumetric data) to represent a three dimensional image of the brain. The annotated whole volume image 700 includes features 705 that, in high definition, may be used to identify a patient. Although the illustrated features 705 of the annotated whole volume image 700 provide an example of features that may be used to identify a patient, there may be additional features in the illustrated annotated whole volume image 700 that may additionally and/or alternatively be used to identify a patient. Additionally, the annotated whole volume image 700 may include metadata and/or the contextual data.

The anonymized image 702 of FIG. 7 is the annotated whole volume image 700 after being anonymized by the image anonymizer 202. As described above in conjunction with FIG. 2, the image anonymizer 202 degrades (e.g., encrypts, downsamples, etc.) the region outside the region of interest 704 to generate a low resolution (e.g., blurred) image outside of the region of interest 704 that cannot be used to identify a patient. For example, as illustrated in the example anonymized image 702, the features 705 from the annotated whole volume image 700 are blurred. The region of interest 704 is fully enclosed in the bounding box 706. The bounding box 706 in the anonymized image 702 remains in high resolution to allow full analysis of the region of interest 704 without identification of the patient, while portion(s) of the image outside the bounding box 706 are provided in low resolution.

Figure 8:
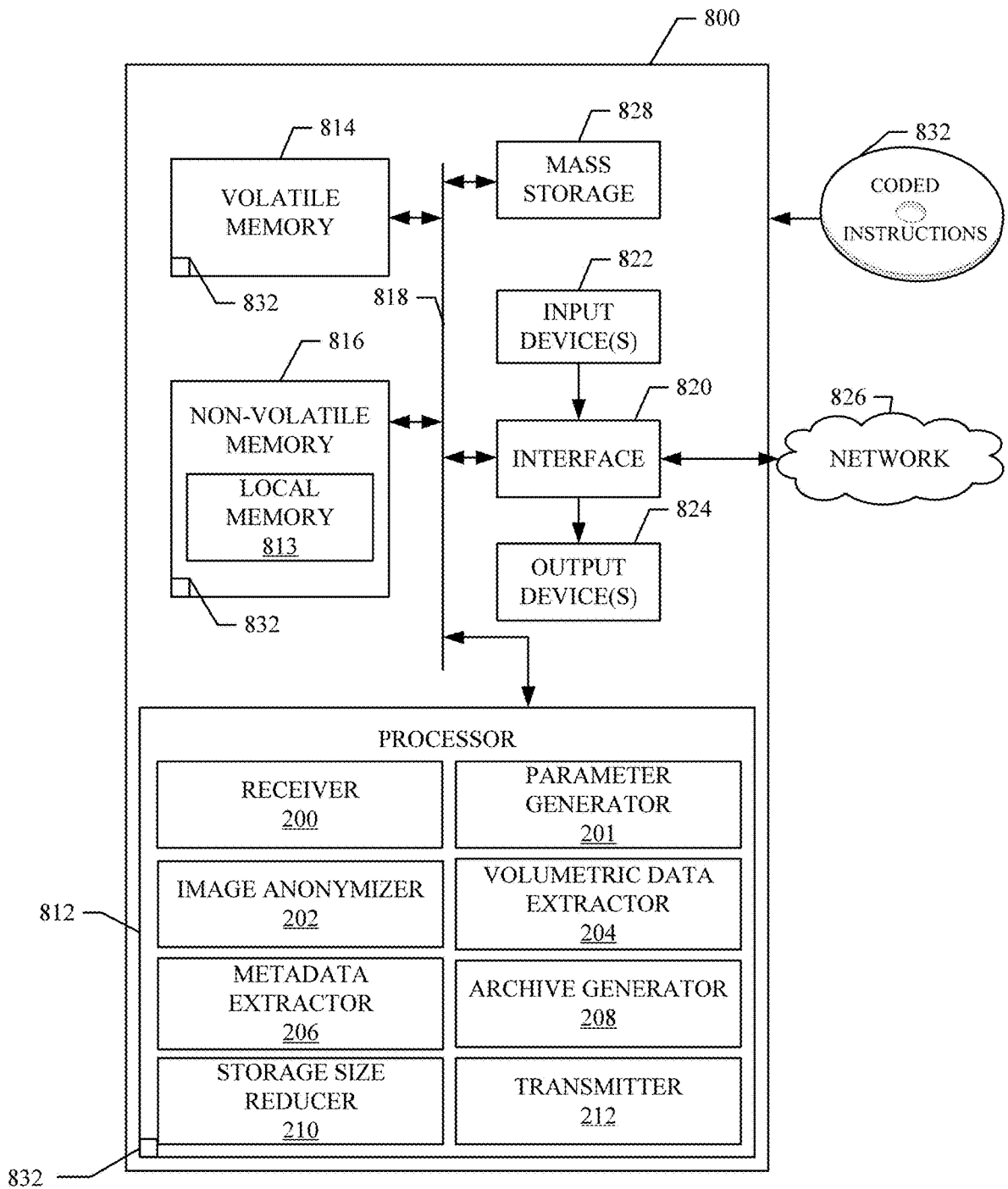
FIG. 8 is a block diagram of a processor platform structured to execute the example machine readable instructions of FIGS. 3 and 4 to implement the example analysis recorder of FIG. 2.

FIG. 8 is a block diagram of an example processor platform 800 structured to executing the instructions of FIG. 8 to implement the analysis recorder 106 of FIGS. 1 and 2. The processor platform 800 can be, for example, a server, a personal computer, a mobile device (e.g., a cell phone, a smart phone, a tablet such as an iPad™), a personal digital assistant (PDA), an Internet appliance, or any other type of computing device.

The processor platform 800 of the illustrated example includes a processor 812. The processor 812 of the illustrated example is hardware. For example, the processor 812 can be implemented by integrated circuits, logic circuits, microprocessors or controllers from any desired family or manufacturer.

The processor 812 of the illustrated example includes a local memory 813 (e.g., a cache). The example processor 812 of FIG. 8 executes the instructions of FIGS. 3 and 4 to implement the receiver 200, the parameter generator 201, the image anonymizer 202, the volumetric data extractor 204, the metadata extractor 206, the archive generator 208, the storage size reducer 210, and/or the transmitter 212 of FIG. 2 to implement the analysis recorder 106. The processor 812 of the illustrated example is in communication with a main memory including a volatile memory 814 and a non-volatile memory 816 via a bus 818. The volatile memory 814 may be implemented by Synchronous Dynamic Random Access Memory (SDRAM), Dynamic Random Access Memory (DRAM), RAIVIBUS Dynamic Random Access Memory (RDRAM) and/or any other type of random access memory device. The non-volatile memory 816 may be implemented by flash memory and/or any other desired type of memory device. Access to the main memory 814, 816 is controlled by a clock controller.

The processor platform 800 of the illustrated example also includes an interface circuit 820. The interface circuit 820 may be implemented by any type of interface standard, such as an Ethernet interface, a universal serial bus (USB), and/or a PCI express interface.

In the illustrated example, one or more input devices 822 are connected to the interface circuit 820. The input device(s) 822 permit(s) a user to enter data and commands into the processor 812. The input device(s) can be implemented by, for example, a sensor, a microphone, a camera (still or video), a keyboard, a button, a mouse, a touchscreen, a track-pad, a trackball, isopoint and/or a voice recognition system.

One or more output devices 824 are also connected to the interface circuit 820 of the illustrated example. The output devices 824 can be implemented, for example, by display devices (e.g., a light emitting diode (LED), an organic light emitting diode (OLED), a liquid crystal display, a cathode ray tube display (CRT), a touchscreen, a tactile output device, and/or speakers). The interface circuit 820 of the illustrated example, thus, typically includes a graphics driver card, a graphics driver chip or a graphics driver processor.

The interface circuit 820 of the illustrated example also includes a communication device such as a transmitter, a receiver, a transceiver, a modem and/or network interface card to facilitate exchange of data with external machines (e.g., computing devices of any kind) via a network 826 (e.g., an Ethernet connection, a digital subscriber line (DSL), a telephone line, coaxial cable, a cellular telephone system, etc.).

The processor platform 800 of the illustrated example also includes one or more mass storage devices 828 for storing software and/or data. Examples of such mass storage devices 828 include floppy disk drives, hard drive disks, compact disk drives, Blu-ray disk drives, RAID systems, and digital versatile disk (DVD) drives.

The coded instructions 832 of FIG. 8 may be stored in the mass storage device 828, in the volatile memory 814, in the non-volatile memory 816, and/or on a removable tangible computer readable storage medium such as a CD or DVD.

From the foregoing, it will be appreciated that the above disclosed methods, apparatus, and articles of manufacture have been disclosed generate an archive based on anonymized analysis results from medical image visualization software. Examples disclosed herein receive a whole volume medical image that is annotated by a clinician. The annotated volume medical image includes a region of interest identified by the clinician. The region of interest corresponds to an irregularity in the whole volume image. Examples disclosed herein anonymize the annotated whole volume image by reducing the resolution and/or blurring the whole volume image outside the region of interest. Examples disclosed herein extract volumetric data, contextual data, and anonymized metadata based on the anonymized whole volume image. Examples disclosed herein generate anonymized archives based on the anonymized whole volume image, the volumetric data, the contextual data, and the anonymized metadata and transmit the anonymized archives to a remote site for further processing.

Due to the large file size of medical image files, some conventional techniques for analyzing medical images include either transmitting the medical images without contextual data or transmitting the contextual data without the medical images. However, such conventional techniques do not anonymize patient data associated with the medical condition and require a large amount of bandwidth to transmit such large medical images. Examples disclosed herein alleviate anonymity and file size problems associated with such conventional techniques by reducing the resolution of the medical images outside of a region of interest and generating a compressed archive based on the lower resolution image which has a significantly smaller size than medical images of conventional techniques.

Some conventional techniques reduce medical image size and anonymize medical images by cropping out the region of a medical image outside the region of interest. However, such cropping techniques do not include contextual data or metadata. Additionally, such cropping techniques remove relative location data (e.g., where the region of interest is in relation to an entire organ). Examples disclosed alleviate such problems by lowering the resolution of the areas outside the region of interest to maintain relative location data while still maintaining a small file size.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. A method comprising:
    anonymizing, by executing an instruction with a processor, a medical image outside of a region of interest based on an extraction parameter by degrading the medical image outside a region corresponding to the region of interest and maintaining a resolution of the medical image inside the region corresponding to the region of interest, wherein the extraction parameter is generated based on at least an image capture parameter; and
    generating, by executing an instruction with the processor, a compressed local archive based on the anonymized medical image.

2. The method of claim 1, wherein: the extraction parameter includes at least one of a second resolution for the second portion, a maximum size of the region of interest, metadata to extract from the medical image, a third resolution for volumetric data, or contextual data to extract from the medical image; and
    the image capture parameter includes at least one of a fourth resolution of the medical image, a body part included in the medical image, a size of the medical image, or device data corresponding to an imaging device that captured the medical image.

3. The method of claim 1, wherein the extraction parameters define how to anonymize the medical image outside the region of interest.

4. The method of claim 1, wherein the anonymizing of the medical image outside of the region corresponding to the region of interest includes degrading the medical image by at least one of blurring the medical image outside the region, masking the medical image outside the region, matching the region to a generic template, encrypting the medical image outside the region, or downsampling voxel values associated with the medical image outside of the region corresponding to the region of interest.

5. The method of claim 4, wherein the extraction parameters define the voxel volume used in at least one the encrypting of the medical image outside the region or the downsampling of the voxel values associated with the medical image outside of the region corresponding to the region of interest.

6. An apparatus comprising:
    a processor to:
    anonymize a medical image outside of a region of interest based on an extraction parameter by degrading the medical image outside a region corresponding to the region of interest and maintaining a resolution of the medical image inside the region corresponding to the region of interest, wherein the extraction parameter is generated based on at least one of an image capture parameter; and
    generate a compressed local archive based on the anonymized medical image.

7. The apparatus of claim 6, wherein: the extraction parameter includes at least one of a second resolution for the second portion, a maximum size of the region of interest, metadata to extract from the medical image, a third resolution for volumetric data, or contextual data to extract from the medical image; and the image capture parameter includes at least one of a fourth resolution of the medical image, a body part included in the medical image, a size of the medical image, or device data corresponding to an imaging device that captured the medical image.

8. The apparatus of claim 6, wherein the extraction parameters define how to anonymize the medical image outside the region of interest.

9. The apparatus of claim 6, wherein the processor is to anonymize the medical image outside of the region corresponding to the region of interest by degrading the medical image by at least one of blurring the medical image outside the region, masking the medical image outside the region, matching the region to a generic template, encrypting the medical image outside the region, or downsampling voxel values associated with the medical image outside of the region corresponding to the region of interest.

10. The apparatus of claim 9, wherein the extraction parameters define the voxel volume used in at least one the encrypting of the medical image outside the region or the downsampling of the voxel values associated with the medical image outside of the region corresponding to the region of interest.

11. The apparatus of claim 6, wherein the processor is to extract data from the medical image and generate the compressed local archive based on the data.

12. A non-transitory computer readable storage medium comprising instructions which, when executed, cause one or more processors to at least:
  anonymize a medical image outside of a region of interest based on an extraction parameter by degrading the medical image outside a region corresponding to the region of interest and maintaining a resolution of the medical image inside the region corresponding to the region of interest, wherein the extraction parameter is generated based on at least an image capture parameter; and
  generate a compressed local archive based on the anonymized medical image.

13. The non-transitory computer readable storage medium of claim 12, wherein: the extraction parameter includes at least one of a second resolution for the second portion, a maximum size of the region of interest, metadata to extract from the medical image, a third resolution for volumetric data, or contextual data to extract from the medical image; and the image capture parameter includes at least one of a fourth resolution of the medical image, a body part included in the medical image, a size of the medical image, or device data corresponding to an imaging device that captured the medical image.

14. The non-transitory computer readable storage medium of claim 12, wherein the instructions cause the one or more processors to anonymize the medical image outside the region of interest.

15. The non-transitory computer readable storage medium of claim 12, wherein the instructions cause the one or more processors to anonymize the medical image outside of the region corresponding to the region of interest by degrading the medical image by at least one of blurring the medical image outside the region, masking the medical image outside the region, matching the region to a generic template, encrypting the medical image outside the region, or downsampling voxel values associated with the medical image outside of the region corresponding to the region of interest.

16. The non-transitory computer readable storage medium of claim 15, wherein the extraction parameters define the voxel volume used in at least one the encrypting of the medical image outside the region or the downsampling of the voxel values associated with the medical image outside of the region corresponding to the region of interest.

17. The non-transitory computer readable storage medium of claim 12, wherein the instructions cause the one or more processors to extract data from the medical image, the archive generate to generate the compressed local archive based on the data.

* * * * *